United States Patent [19]
Weil et al.

[11] Patent Number: 6,055,447
[45] Date of Patent: *Apr. 25, 2000

[54] PATIENT $CO_2$ MEASUREMENT

[75] Inventors: Max Harry Weil, Northbrook, Ill.; Wanchun Tang, Palm Desert; Jose Bisera, Camarillo, both of Calif.

[73] Assignee: Institute of Critical Care Medicine, Palm Springs, Calif.

[*] Notice: This patent is subject to a terminal disclaimer.

[21] Appl. No.: 09/099,293

[22] Filed: Jun. 18, 1998

Related U.S. Application Data

[63] Continuation-in-part of application No. 08/939,591, Sep. 29, 1997, which is a continuation-in-part of application No. 08/710,208, Sep. 13, 1996, which is a continuation-in-part of application No. 08/498,932, Jul. 6, 1995, Pat. No. 5,579,763.

[51] Int. Cl.[7] ............................................. A61B 5/00
[52] U.S. Cl. ............................................. 600/353; 600/309
[58] Field of Search ................................ 600/345–350, 600/309, 300, 301, 587, 529, 353, 354

[56] References Cited

U.S. PATENT DOCUMENTS

| | | |
|---|---|---|
| 3,905,889 | 9/1975 | Macur et al. . |
| 4,016,863 | 4/1977 | Brantigan . |
| 4,381,011 | 4/1983 | Somers, 3rd . |
| 4,503,859 | 3/1985 | Petty et al. . |

(List continued on next page.)

FOREIGN PATENT DOCUMENTS 9423645  10/1994  WIPO .................................. 600/345

OTHER PUBLICATIONS

Jin et al. (1997), "End–Tidal $PCO_2$ Serves as an Indicator of Cardiac Output During Experimental Septic Shock," *Crit. Care Med.* 25(1):A122 (Abstract).

Nakagawa et al. (1997), "Sublingual Capnometry for Quantitation of the Severity of Hemorrhagic Shock," *Shock* 7:14 (Abstract).

Nakagawa et al. (1997), "$ETCO_2$ as Non–Invasive Indicator of Cardiac Output During Hemorrhagic Shock," *Crit. Care Med.* 25(1):A132 (Abstract).

Nakagawa et al. (1997), "Sublingual Capnography as an Indicator of Perfusion Failure In Human Patients," *Chest* 112:4S (Abstract).

Nakagawa et al. (1998), "Comparison of Sublingual Capnometry with Gastric Capnometry and Lactate as Indicators of the Severity of Hemorrhagic Shock," *Crit. Care Med.* 26(1):A44 (Abstract).

(List continued on next page.)

*Primary Examiner*—Robert L. Nasser
*Attorney, Agent, or Firm*—Dianne E. Reed; Reed & Associates

[57] ABSTRACT

A method and apparatus are provided for assessing impairment of blood circulation of a patient by measurement of $PCO_2$ (partial pressure of carbon dioxide) in the upper digestive/respiratory tract of the patient. The method includes introducing a $CO_2$ sensor into the mouth-nose area and against a mucosal surface. In one example, the sensor is placed under the tongue, in the manner of an oral thermometer, and sublingual (under the tongue) measurements of $CO_2$ are taken. This allows for the triage of patients or victims in emergency of disaster settings. The measurement involves minimal invasion while avoiding false readings. For monitoring of more than about one or two minutes, holders are used to hold the $CO_2$ sensor instrument stabily in the mouth or nose, and to isolate the mucosal area immediately around the $CO_2$ sensor from air flow that could carry away $CO_2$, while maintaining high humidity.

6 Claims, 7 Drawing Sheets

U.S. PATENT DOCUMENTS

| | | |
|---|---|---|
| 4,535,786 | 8/1985 | Kater . |
| 4,577,109 | 3/1986 | Hirschfeld . |
| 4,632,119 | 12/1986 | Reichstein . |
| 4,643,192 | 2/1987 | Fiddian-Green . |
| 4,729,824 | 3/1988 | Giner . |
| 4,785,814 | 11/1988 | Kane . |
| 4,789,453 | 12/1988 | Eberhard et al. . |
| 4,816,131 | 3/1989 | Bomsztyk . |
| 4,833,091 | 5/1989 | Leader et al. . |
| 4,834,101 | 5/1989 | Collison et al. . |
| 4,842,783 | 6/1989 | Blaylock . |
| 4,890,619 | 1/1990 | Hatschek . |
| 4,892,383 | 1/1990 | Klainer et al. . |
| 4,919,891 | 4/1990 | Yafuso et al. . |
| 4,981,470 | 1/1991 | Bombeck, IV . |
| 5,006,314 | 4/1991 | Gourley et al. . |
| 5,098,659 | 3/1992 | Yim et al. . |
| 5,105,812 | 4/1992 | Corman . |
| 5,117,827 | 6/1992 | Stuebe et al. . |
| 5,158,083 | 10/1992 | Sacristan et al. . |
| 5,174,290 | 12/1992 | Fiddian-Green . |
| 5,251,619 | 10/1993 | Lee .......................................... 600/309 |
| 5,280,548 | 1/1994 | Atwater et al. . |
| 5,329,922 | 7/1994 | Atlee, III . |
| 5,330,718 | 7/1994 | Hui et al. . |
| 5,341,803 | 8/1994 | Goldberg et al. . |
| 5,368,027 | 11/1994 | Lübbers et al. . |
| 5,408,999 | 4/1995 | Singh et al. . |
| 5,411,022 | 5/1995 | McCue et al. . |
| 5,423,320 | 6/1995 | Salzman et al. . |
| 5,453,248 | 9/1995 | Olstein . |
| 5,456,251 | 10/1995 | Fiddian-Green . |
| 5,479,923 | 1/1996 | Rantala . |
| 5,579,763 | 12/1996 | Weil et al. ............................... 600/345 |
| 5,596,988 | 1/1997 | Markle et al. . |
| 5,631,340 | 5/1997 | Olstein . |
| 5,714,121 | 2/1998 | Alderete et al. . |
| 5,743,259 | 4/1998 | Kruse ...................................... 600/309 |
| 5,788,631 | 8/1998 | Fiddian-Green . |

OTHER PUBLICATIONS

Ogino et al. (1994), "Reflectance Pulse Oximeter Measuring Central SaO2 From Mouth," *Proceedings of the Annual International Conference of the IEEE Engineering in Medicine and Biology Society*, Baltimore, 2(16):914–915.

Peterson et al. (1984), "Fiber Optic Sensors for Biomedical Applications," *Science* 224(4645):123–127.

Sato et al. (1997), "Esophageal and Gastric $PCO_2$ Both Serve as Quantitative Indicators of Organ Blood Flow During Hemorrhagic Shock," *Crit. Care Med.* 25(1):A37 (Abstract).

Sato et al. (1997), "Esophageal $PCO_2$ as a Monitor of Perfusion Failure During Hemorrhagic Shock," *J. Appl. Physiol.* 82(2):558–562.

Seitz (1984), "Chemical Sensors Based on Fiber Optics," *Anal. Chem.* 56(1):16A–34A.

Tang et al. (1988), "Myocardial Preservation During Cardiopulmonary Resuscitation," *Curr. Opin. Crit. Care* 4:155–160.

Vurek et al. (1983), "A Fiber Optic $PCO_2$ Sensor," *Annals Biomed. Engineer.* 11:499–510.

Weil (1998), "The Assault on the Swan–Ganz Catheter," *Chest* 113:1379–1386(1998) (Invited Publication).

Xie et al. (1997), "Sublingual Capnometry for Quantitation of the Severity of Septic Shock," *Shock* 7:13–14 (Abstract).

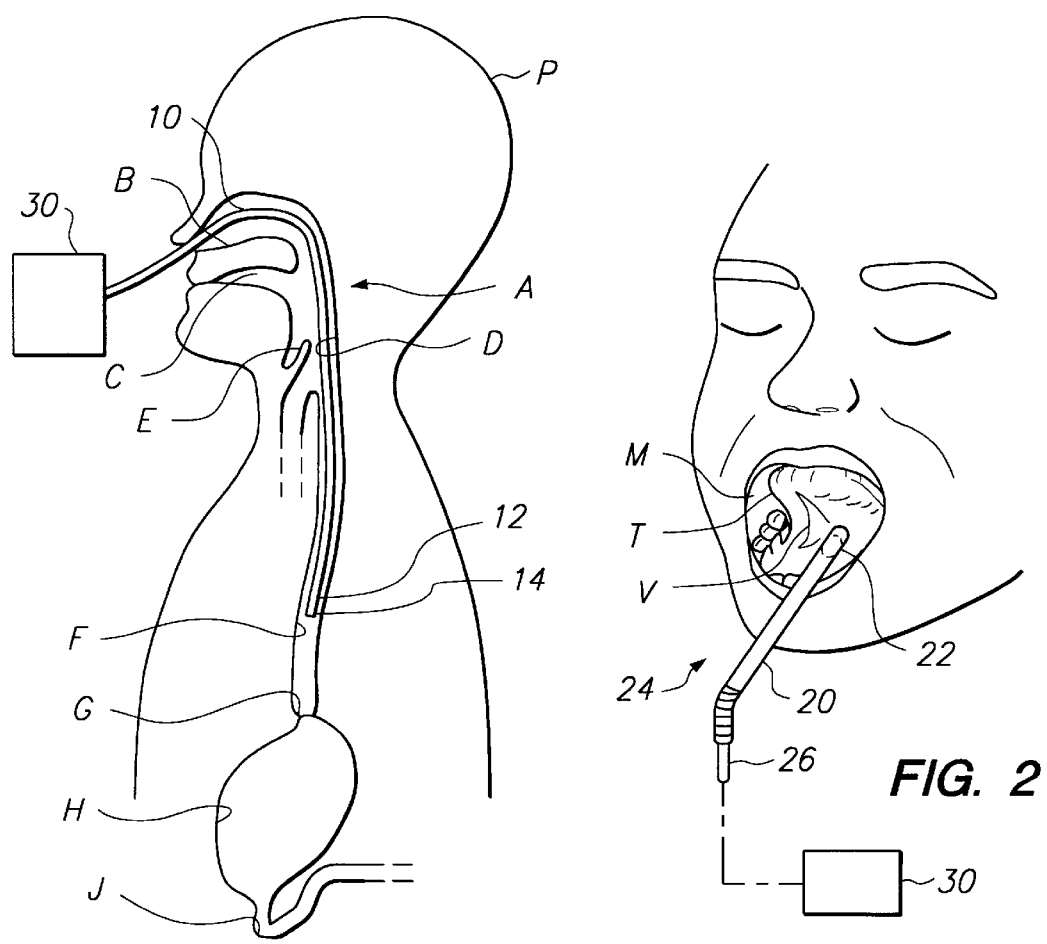
FIG. 1
FIG. 2
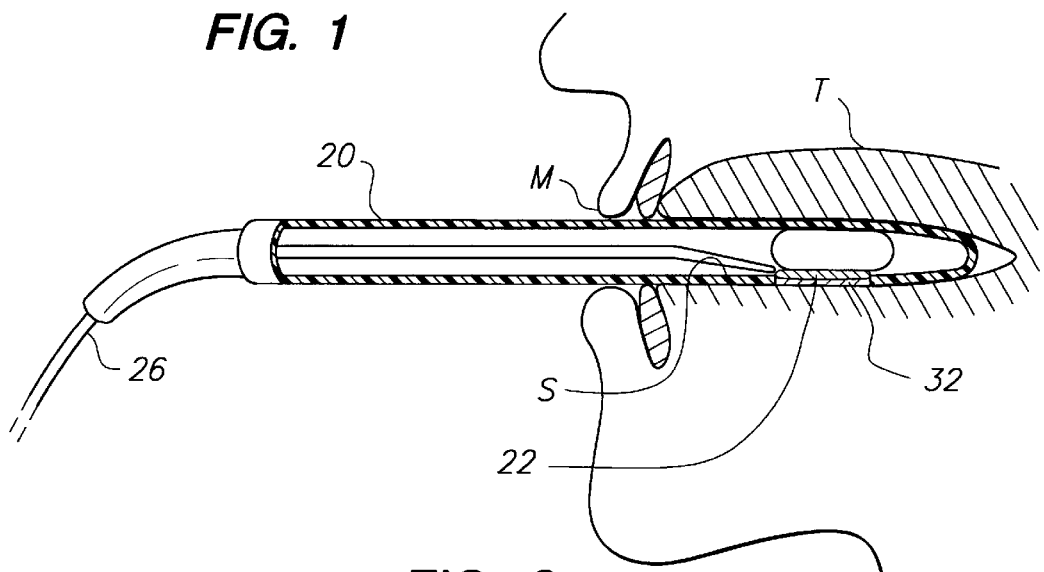
FIG. 3

PATIENT CO₂ MEASUREMENT

CROSS-REFERENCE TO RELATED APPLICATIONS

This application is a continuation-in-part of U.S. application Ser. No. 08/939,591, filed Sep. 29, 1997, which was as a continuation-in-part of U.S. application Ser. No. 08/710,208, filed Sep. 13, 1996, which was a continuation-in-part of U.S. application Ser. No. 08/498,932 filed Jul. 6, 1995, now U.S. Pat. No. 5,579,763.

BACKGROUND OF THE INVENTION

Very low systemic perfusion (flow of blood) is caused by potentially reversible hemorrhage, sepsis (spread of bacteria) and cardiac arrest. When there is very low blood flow, generally due to low aortic pressure, the body directs a greater percentage of the flow to the brain and other organs that require continuous blood flow to survive (although the flow decreases even to such critical organs), while greatly decreasing the flow to other organs and tissues which can survive for a longer time without large blood flow. When perfusion to these less critical organs and tissues such as the stomach decreases, carbon dioxide resulting from metabolism is not rapidly carried away and the partial pressure of carbon dioxide increases. The measurement of $CO_2$ and changes in pH resulting therefrom, are commonly made in the stomach and intestines to determine the extent of perfusion failure in a patient and to determine the effectiveness of treatment.

The measurement of $CO_2$ is commonly made by threading a catheter through the nasal passage and the esophagus to the stomach, and sometimes through the stomach into the intestines, with a catheter sometimes being threaded through the anus into the colon. These procedures are invasive and can harm the patient.

In U.S. Pat. No. 5,579,763, applicants describe the introduction of a catheter with a carbon dioxide sensor through the nasal or oral passage into the esophagus. That patent presents the results of tests showing that measurements of $CO_2$ in the esophagus are closely correlated with aortic pressure and they are even better correlated to aortic pressure than measurements of $CO_2$ in the stomach. While $CO_2$ measurements in the esophagus involve only moderate invasiveness, it is still invasive to the body since it involves moving a catheter down past the epiglottis to reach the esophagus. It would be desirable if an even less invasive method were available to measure perfusion failure and to indicate the state of the patient as a result of perfusion failure and as the result of blood infusion or other methods taken to increase perfusion.

SUMMARY OF THE INVENTION

In accordance with one embodiment of the present invention, a method is provided for assisting in the measurement of perfusion failure of a patient, based upon measurement of $CO_2$ in the digestive/respiratory system of a patient, which is minimally invasive. The method includes introducing a carbon dioxide sensor into the upper digestive/respiratory tract of a patient, without passing the sensor down through or beyond the epiglottis of the patient. By avoiding passage through the mouth into the throat and food pipe (esophagus), both discomfort from and injury to these structures is avoided. Specifically a carbon dioxide sensor is placed against a mucosal surface of the mouth or nose. Applicant has discovered that increases in $CO_2$ of tissues is a phenomenon universal to the body.

Applicant prefers to introduce the carbon dioxide sensor sublingually, or under the tongue, and preferably to one side of the frenulum. The invasiveness is minimal, being substantially no more than in the use of an oral thermometer. The sensor preferably lies at the inner end of a holder that lies stably in the patient's mouth. The holder not only maintains the sensor position, but isolates the area immediately around the mucosal surface engaged by the sensor, from surrounding air flow that could carry away some $CO_2$. The output of the sensor can drive a circuit that senses the rate of change of $CO_2$ with time and the level of $CO_2$ to indicate the patient's condition. Applicant may use a holder that holds a carbon dioxide sensor between a lip and the teeth, or in the nose. The holder may be constructed to introduce moisture into the isolated region where the sensor contacts a mucosal surface.

The novel features of the invention are set forth with particularity in the appended claims. The invention will be best understood from the following description when read in conjunction with the accompanying drawings.

BRIEF DESCRIPTION OF THE DRAWINGS

FIG. 1 is a partial sectional view of the digestive system of a patient (including the nasal passage), and showing a previous sensor of applicant which is fully installed during a test.

FIG. 2 is an isometric view showing a sensor of the present invention as it is introduced into the mouth of a patient, for sublingual placement.

FIG. 3 is a sectional view showing the sensor of FIG. 2 fully installed in a patient's mouth.

DESCRIPTION OF THE PREFERRED EMBODIMENTS

Figure 4:
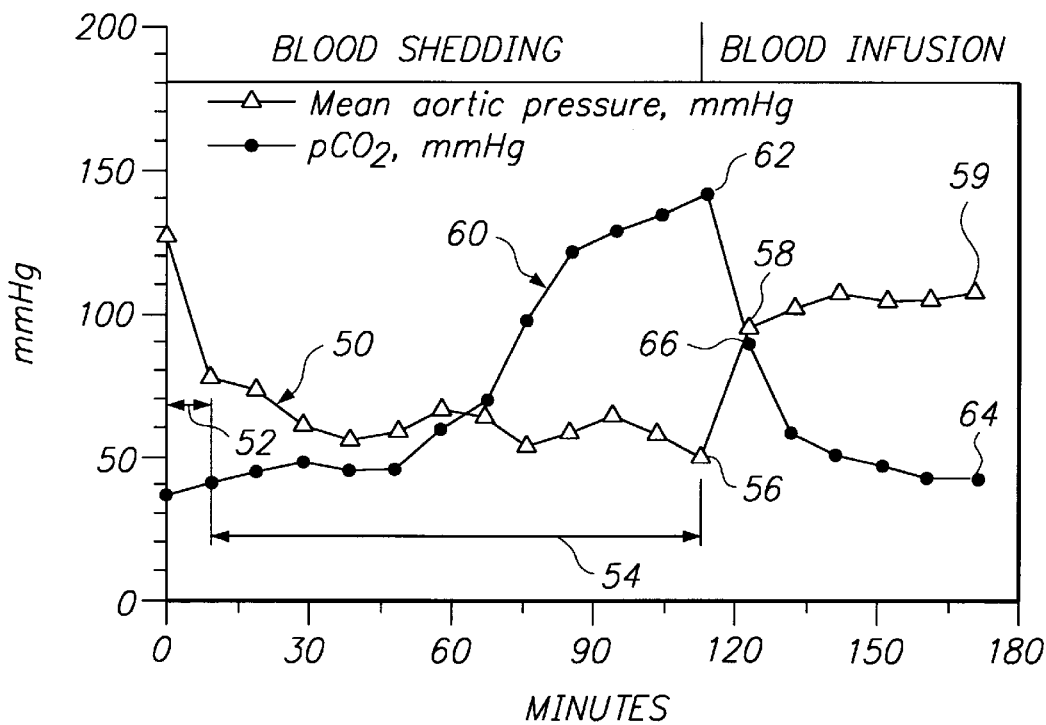
FIG. 4 is a graph that includes a graph line showing variation in aortic pressure with time, and that also includes a graph line showing variation in sublingual $pCO_2$ measurement with time, during an experiment on a rat.

FIG. 1 illustrates the upper digestive/respiratory system or tract A of a person, including the nasal and oral passages B, C and the upper portion D of the throat that extends to the top of the epiglottis E. The gastrointestinal or digestive tract also includes the esophagus F, the esophageal sphincter G, the stomach H, and the intestines J. It is known that blood vessels (not shown) which carry blood to the walls of the stomach and intestines, experience severely reduced perfusion in the event of perfusion failure. That is, when there is a reduced flow of blood from the heart, the body directs a higher portion of blood to organs such as the brain which will not survive long without a continuous supply of blood, while restricting the flow to the stomach and intestines whose survival is not threatened by a temporary large reduction in blood flow. As a result, it is common for physicians to assess perfusion failure by taking measurements in the stomach and intestine which indicate the level of blood flow thereat. A useful measurement is the partial pressure of carbon dioxide $CO_2$. Even with low blood flow, metabolism continues, producing $CO_2$ that is not rapidly carried away in the blood flow. Therefore, a large partial pressure of $CO_2$ indicates perfusion failure. It is noted that an increase in $CO_2$ results in a decrease in pH and it is therefore common to measure the pH in the stomach and intestines for quantitating perfusion failure.

Measurements of $CO_2$ in the stomach or intestines has potentially unfavorable side effects, including trauma or harm to the patient caused by insertion of a catheter with a $CO_2$ sensor past the epiglottis, through the esophagus, past the esophageal sphincter, and into the stomach. Such insertion is also complex.

Applicant earlier found that he obtains an accurate assessment of perfusion failure by measuring the partial pressure of $CO_2$ in the esophagus of a patient, instead of only in the stomach and/or intestine of a patient. Earlier measurements involved the insertion of a catheter 10 (FIG. 1) with a $CO_2$ sensor 12 at the end, through the nasal or oral passage B, C, past the epiglottis E, and into the esophagus F. The end 14 of the catheter with the sensor 12 thereat, both lay within the esophagus. Advantages of this procedure were reduced invasion of the patient and that $CO_2$ generated in the stomach by digestion fluids did not affect the measurement of $CO_2$ since the esophageal sphincter blocks such gas. However, the insertion of the catheter past the epiglottis E and into the esophagus, still constituted considerable invasion. In addition to harm that might be caused by threading the catheter into place, the fact that the catheter extended past the epiglottis E meant that the patient would also be exposed to the risk of regurgitation of stomach contents including stomach acids.

In accordance with the present invention, applicant finds that a highly useful measurement of perfusion failure can be obtained by measuring $CO_2$ in the upper digestive/respiratory tract A, with the sensor lying above the epiglottis E so it does not have to pass by it. The $CO_2$ sensor lies against a mucosal surface in the upper digestive/respiratory tract A, in order that it effectively measures $CO_2$ in the tissue. A mucosal surface is a surface of a membrane containing mucus secreting glands, such surface lining body passages and organs that are open to external infection, and being principally located along the digestive and respiratory tracts. Carbon dioxide can readily pass through mucosal surfaces, so that metabolic activity occurring in tissue below the mucosal surface, results in the generation of $CO_2$ which readily migrates through the mucosal surface if not carried away by blood flow. Applicant finds that a $CO_2$ sensor placed against a mucosal surface of the upper digestive/respiratory tract A provides a very good quantification of perfusion failure at all times, including the most critical minutes after the onset of perfusion failure when treatment is likely to be most effective.

FIG. 2 shows a method of the present invention, wherein a tube 20 containing a $CO_2$ sensor 22 at its front end, is inserted into the oral passage and placed under the tongue T of the patient, preferably to one side of the frenulum V. After insertion, it would be desirable if the mouth M of the patient is kept closed around the tube, so air does not circulate around the $CO_2$ sensor, which carries away some carbon dioxide. However, with other instruments commonly inserted through the mouth, and with a patient in a critical condition, the patient is usually unable to keep his mouth closed. Also, when the patient breathes through his nose, there is some air flow around the mouth.

The tube 20 and sensor 22 are part of an instrument 24 that includes a flexible cable 26 that extends to a test instrument 30 that typically indicates the partial pressure of $CO_2$ as in millimeters of mercury (mmHg) to thereby indicate the degree of perfusion failure. While the tube 20 is substantially rigid, the cable 26 is flexible. The cable 26 can be made highly flexible for ease of use, instead of having only the moderate flexibility of a catheter. A catheter (of the prior art) requires some flexibility to pass through curved body passages but must be resistant to column-type collapse, in order that an insertion force at the proximal end of the catheter enables the distal end to be pushed along the body passage. Since the cable 26 does not have to be pushed, it can have more flexibility for ease of use. The largely rigid tube 20 preferably has a length of no more than about one foot (one-third meter), since a longer length would be cumbersome. Catheters for insertion through the esophagus into the stomach, generally have a length of much more than two feet. FIG. 3 shows an example of a sensor 22, which lies against a membrane 32 which is in contact with the sublingual mucosal surface.

FIG. 4 shows the results of an animal test that simulates a sudden loss or shedding of blood, such as might be caused by a gunshot wound or other severe wound, later followed by treatment such as blood infusion. Graph 50 is a measure of mean aortic pressure in mmHg throughout the test. Graph 60 is a measure of sublingual (under the tongue) $pCO_2$ obtained by a sensor.

At the beginning of the test, considerable blood was drawn from an animal that was previously in good health, the blood being drawn within a period of a few minutes, indicated by the graph portion 52 of graph 50, which shows that aortic pressure rapidly dropped about 30% during the first few minutes of the test. In a subsequent period 54 of about two hours, the aortic pressure remained about 40% below normal. The graph 60, which shows the partial pressure of $CO_2$ under the tongue of the subject, shows that the partial pressure of $CO_2$ increased about 35% during the first 30 minutes, while aortic pressure 50 decreased by about 40%. From about 50 minutes to 120 minutes, the partial pressure of $CO_2$ rapidly increased until at 62, the $pCO_2$ had increased by 300% above its initial value. At 120 minutes, blood was infused into the subject and its aortic pressure rapidly increased, from point 56 to point 58 and then point 59, to about 90% of its original pressure before the test. The partial pressure of $CO_2$ rapidly decreased from point 62, which was 300% above normal, to point 64, which was only 25% above normal.

If the chart of FIG. 4 is considered to represent a person suffering an injury such as a gunshot wound or a severe cut from machinery or a knife, the graph 50 would represent the fact that aortic pressure rapidly decreases during blood loss, until the outflow of blood is stopped by a paramedic or other person applying pressure to stop bleeding. It may take perhaps thirty minutes for the patient to reach a hospital and be checked by a physician. If the physician places a $CO_2$ sensor under the tongue of the patient and monitors the $CO_2$ measurement, the physician will see that the carbon dioxide level is rapidly increasing and is considerably above normal. The rapid increase suggests a loss of blood within the last hour or so, while the high level of $CO_2$ indicates the low level of aortic pressure and perfusion failure. If the physician, paramedic or other emergency provider determines that a transfusion of blood or blood components is indicated, and the transfusion results in a rapid increase of aortic pressure, as from point 56 to point 58, then this will be indicated by the rapid drop in $pCO_2$ from point 62 to point 66. It is noted that the aortic pressure increases only moderately thereafter until it stabilizes while there is a delay before stabilization of the $CO_2$ pressure. This is due to the delay before increased blood flow results in the removal of carbon dioxide from the tissue. The graph 60 of FIG. 4 shows that the sublingual measurement of $CO_2$ provides a good indication of the level of perfusion failure.

Figure 5:
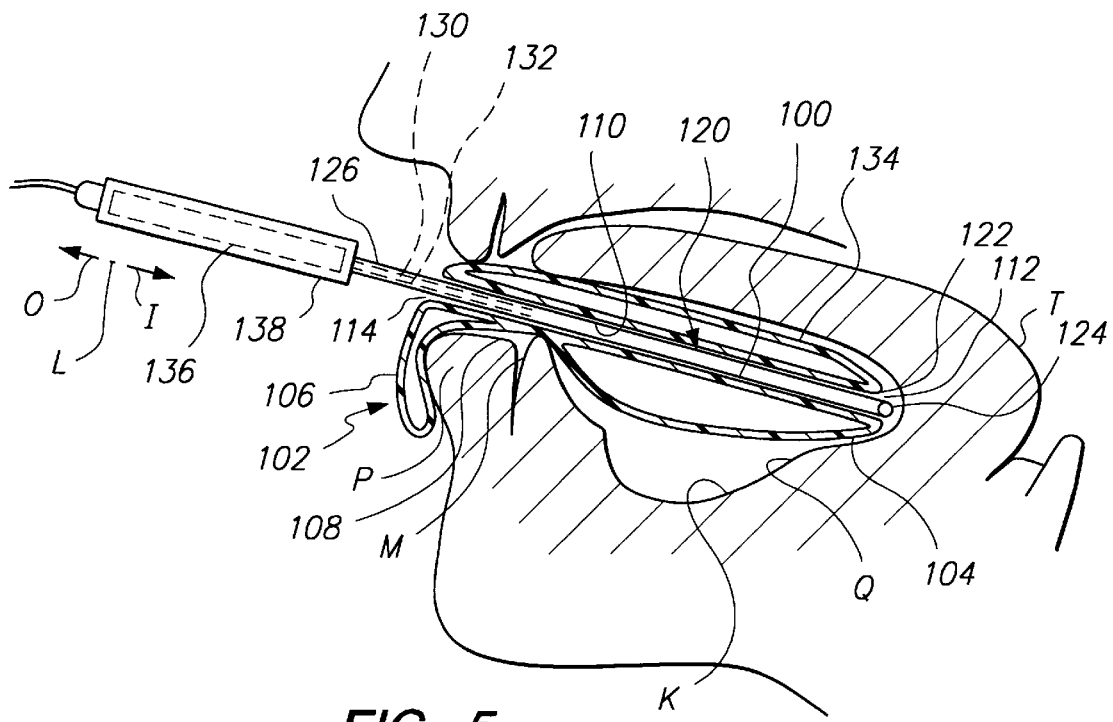
FIG. 5 is a sectional view of a sensor assembly and holder constructed in accordance with another embodiment of the invention, shown lying in a patient's mouth.

FIG. 5 shows a sensor assembly instrument 100 that is held in position by a sensor holder 102 that lies primarily in a patient's mouth. The sensor holder has a sublingual inner portion 104 that is shaped to fit under the patient's tongue T, and especially near the location where the tongue merges with the bottom or floor K of the mouth, and to lie on the bottom of the mouth. The holder has an outer portion 106 that lies outward of the inner portion and that is accessible from outside the mouth. The particular outer portion 106 lies outside the mouth and has a laterally (L) extending groove or recess 108 with groove walls that rest on the lower denture M and lower lip P of the patient.

The holder 102 forms a holder passage 110 that extends between the inner and outer portions 104, 106 of the holder. The passage has at least inner and outer ports 112, 114 and preferably extends along the entire length of the holder in the inner and outer directions I, O. The sensor assembly 100 has a frame 120 with an inner end 122 that supports a $CO_2$ sensor 124. The sensor 124 projects inwardly from the holder and directly contacts the mucosal surface Q of the patient. The frame has an outer end 126 that lies outside the patients mouth. A pair of electrical conductors or wires 130, 132 extend in the frame along the length of the passage between the sensor and an electrical circuit portion 136 mounted in a handle 138, the circuit portion 136 preferably being a preamplifier but possibly being only a connector.

The holder 102 serves two important purposes. Perhaps the most important purpose is to isolate the mucosal surface area at and immediately around (within about a centimeter or two) the location where the sensor touches the mucosal surface Q, from air flows in the mouth. Such isolation traps moisture from the mucosal surface or from a device that adds moisture to the area where measurements are taken. As discussed above, such air flows can sweep away some of the $CO_2$, resulting in a lower reading. The entrapment of submucosal $CO_2$ by the holder avoids such effect. To this end, the sublingual inner portion 104 of the holder preferably lies close to the walls of the mouth on opposite sides of the sensor 124, as well as above and below the sensor. The upper surface 134 of the holder is designed so the tongue T can lie on at least its inner portion, to further provide a seal and to support the tongue to avoid tiring the patient.

A second purpose of the holder is to fix the position of the sensor assembly 100 and the sensor 124 thereof so the sensor does not move during an extended period of many minutes or even hours while the $CO_2$ of the patient is being measured. A tension coil spring extending between the handle and holder, can be used to gently urge the frame 120 inwardly, where necessary. The holder 102 is preferably formed of an elastomeric material (Young's modulus less than 50,000 psi) such as a soft rubber or soft foam, to more readily fit the particular patient's mouth and to avoid high localized pressure on the patient's mouth that could discomfort him or her.

A third possible function is to add moisture to the area where measurements are taken. It should be noted that in the triage of a fully alert patient, the $CO_2$ sensor may be used without a holder or humidification, for a period of about one to two minutes.

Figure 6:
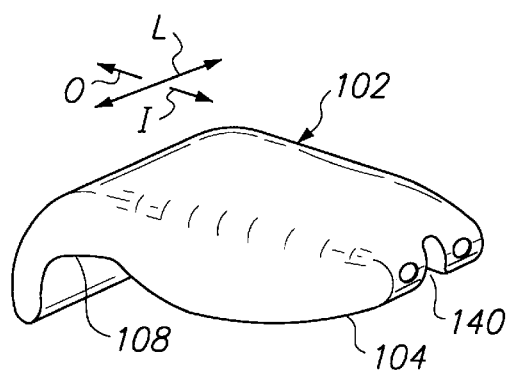
FIG. 6 is an inner isometric view of the holder of FIG. 5.
Figure 7:
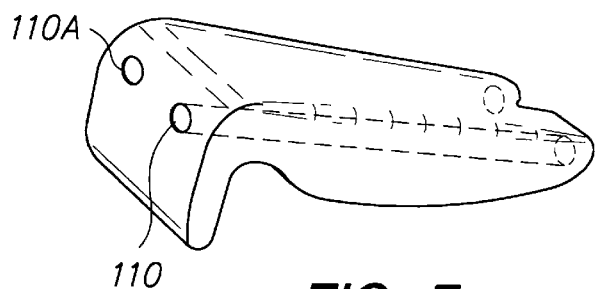
FIG. 7 is an outer isometric view of the holder of FIG. 5.

FIGS. 6 and 7 show that the holder 102 is preferably formed with a slot 140 that receives the frenulum of the tongue, so the sublingual inner portion 104 can lie close to the inner end of the sublingual area and therefore closely around the $CO_2$ sensor. The particular holder shown has two passages 110, 110A that lead to areas on opposite sides of the frenulum. A thermometer can be inserted through the second passage, as the level of $CO_2$ is slightly affected by the patient's temperature. A thermometer can be incorporated in the instrument that includes the carbon dioxide sensor.

Figure 8:
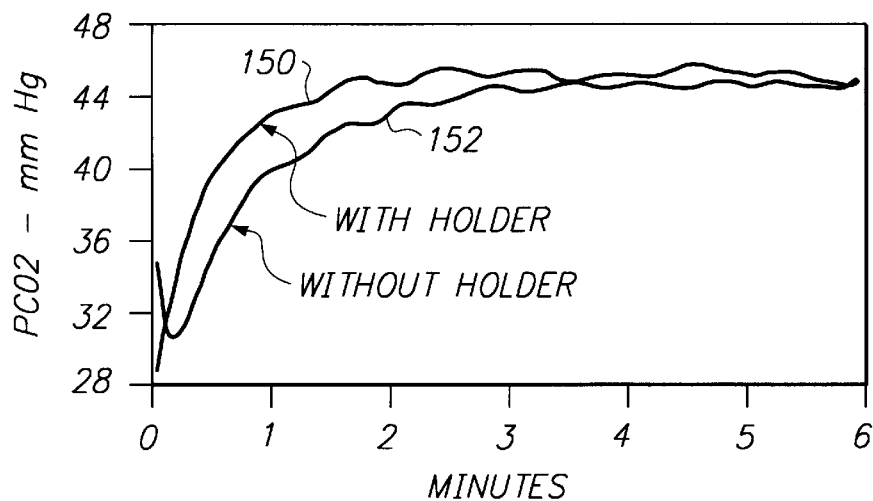
FIG. 8 is a graph that includes graph lines showing sublingual response with and without the holder of FIG. 5.

FIG. 8 is a graph showing the partial pressure of carbon dioxide in millimeters of mercury, versus time in minutes, when the holder 102 was used and when the holder was not used. The tests were conducted using a healthy human volunteer who kept his mouth closed (around the holder and instrument) throughout the test, breathing only through his nose. Graph line 150 shows the results when the holder was used, while graph line 152 shows the results when the holder was not used. It can take a few minutes for the sensed level of carbon dioxide to reach a steady state. It can be seen that the graph line 150, showing results when the holder was used, reached a steady state condition after about two minutes, while the graph line 152, showing results without the holder, reached a steady state condition after about three minutes. Also, it can be seen that the measured level at 150 when the holder was used, is somewhat higher. This represents the fact that much less carbon dioxide was removed from the mucosal surface engaged by the sensor, by air flowing past it as a result of air flow through the nose. An ill patient might not keep his mouth closed, resulting in a greater difference.

Figure 9:
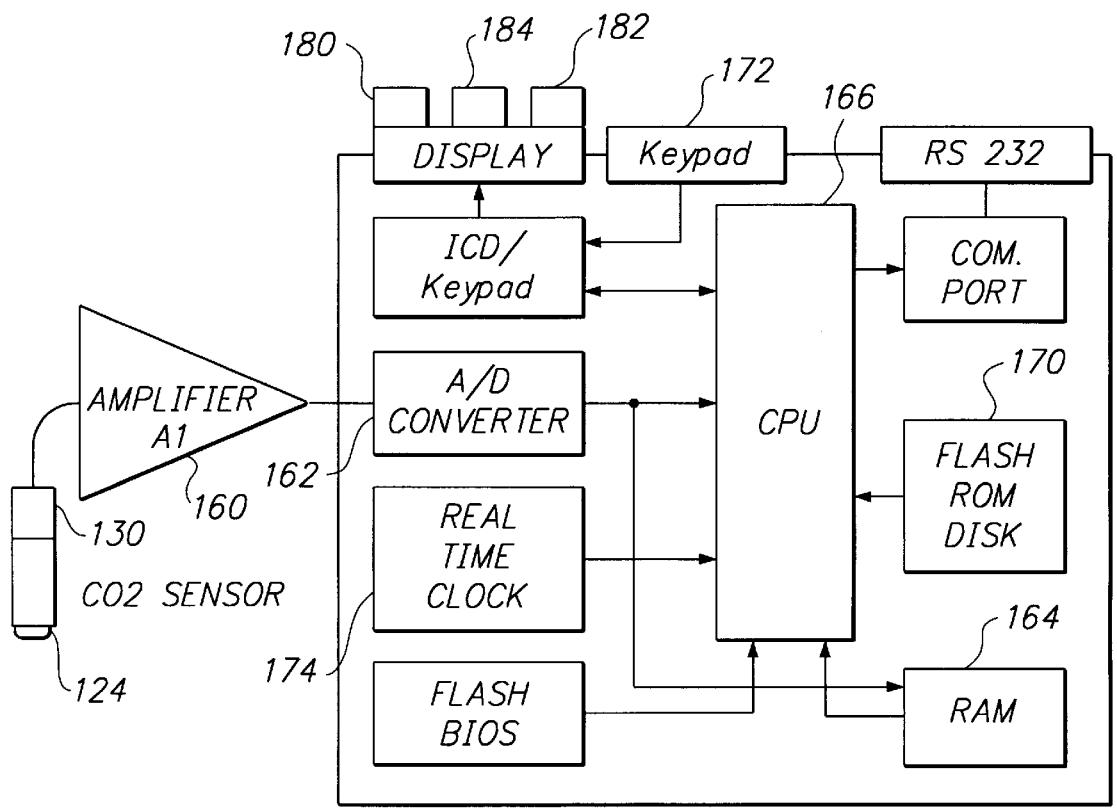
FIG. 9 is an electrical block diagram of a circuit for processing data that includes the output of the $CO_2$ sensor of FIG. 5.

FIG. 9 shows data acquisition circuitry that facilitates analysis of the $CO_2$ data. The circuit includes preamplifier 130 and amplifier 160, which deliver signals representing the $CO_2$ level to an A/D converter 162. The converter output is delivered to a memory 164 which stores the values and delivers them to a CPU, or central processing unit 166. Software for instructing the CPU to operate on the data, is contained in a memory disk 170. Pertinent information such as characteristics of the patient can be inputted through a keyboard 172.

$CO_2$ levels are delivered to the CPU at a rate of five samples per second. The CPU uses this data and the elapsed time from a clock 174 to deliver signals indicating the perfusion state of the patient. If the patients condition is poor, a red light 180 is illuminated, if the patient's condition is stable a green light 182 is illuminated, and if the patient's condition is guarded a yellow light is illuminated 184. This simplistic output is useful for moderately skilled persons such as medics in the armed forces and paramedics on ambulances. An indication of the patient's condition enables the health worker to determine whether or not the patient should be rushed to a treatment center and/or whether certain steps should be taken to enhance perfusion such as repeated depression of the chest.

Figure 10:
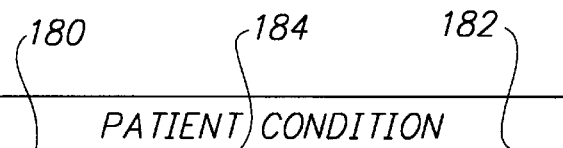
FIG. 10 is a chart that shows the logic of the circuit of FIG. 9.

FIG. 10 indicates the basic principles on which the software controls the CPU to determine which of the three signals (red light, green light or yellow light) to give. A particular high level of carbon dioxide Z which may be, for example 80 mm Hg is established, as well as a low level Y such as 50 mm Hg. In addition, the CPU continually determines the rate of increase or decrease of $pCO_2$. If the $pCO_2$ is increasing at a rate of more than 20 mm Hg/hr., this will have a very negative implication. If the rate of change of $pCO_2$ is less than 20 mm Hg/hr., then this is moderately negative or neutral. If the $pCO_2$ level is decreasing, or negative, this is usually positive.

In the chart of FIG. 10, a first category 190 is for patients having a $pCO_2$ greater than Z. If the rate of change Of $pCO_2$ is zero or positive, then the condition of the patient is assessed as being poor and the red light at 180 is energized. If the $pCO_2$ is decreasing, then the yellow light 184 is energized to indicate that the patient is in a guarded state. A similar procedure is used for the case 192 where the partial pressure of carbon dioxide is between the two levels Z and Y. In that case the patient's condition is guarded and the yellow light is energized unless the $pCO_2$ level is increasing at more than 20 mm Hg/hr. in which case the red light is energized. For the third category 194, the carbon dioxide level is less than Y, and the patient is deemed to be in a stable condition, unless there is a considerable change in carbon dioxide, that is, the level is increasing at more than 20 mm Hg/hr. or is decreasing at more than a certain rate such as 10 mm Hg/hr. It is noted that with the carbon dioxide level less than Y, a considerable change in carbon dioxide level may indicate that something else is wrong with the patient.

Figure 11:
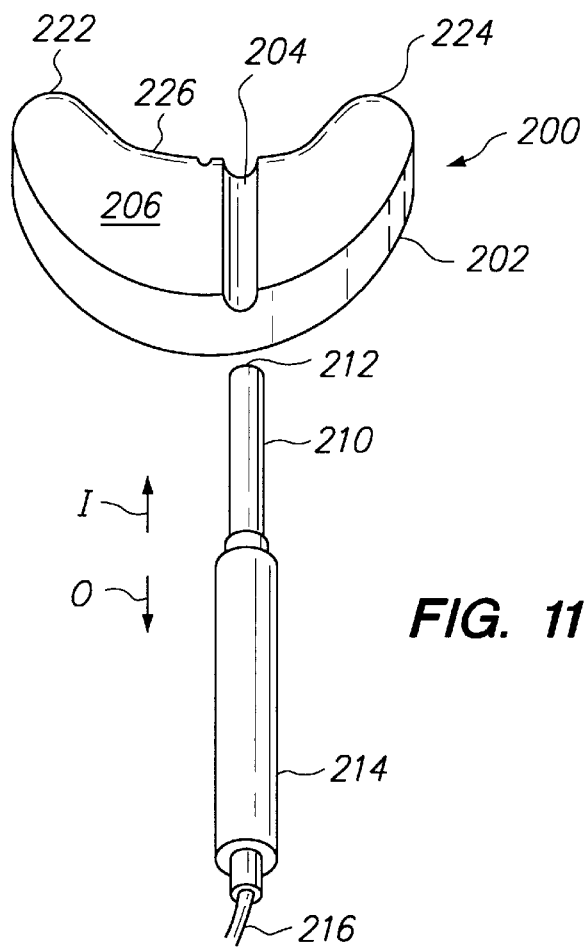
FIG. 11 is a top and outer isometric view of a holder of another embodiment of the invention.
Figure 12:
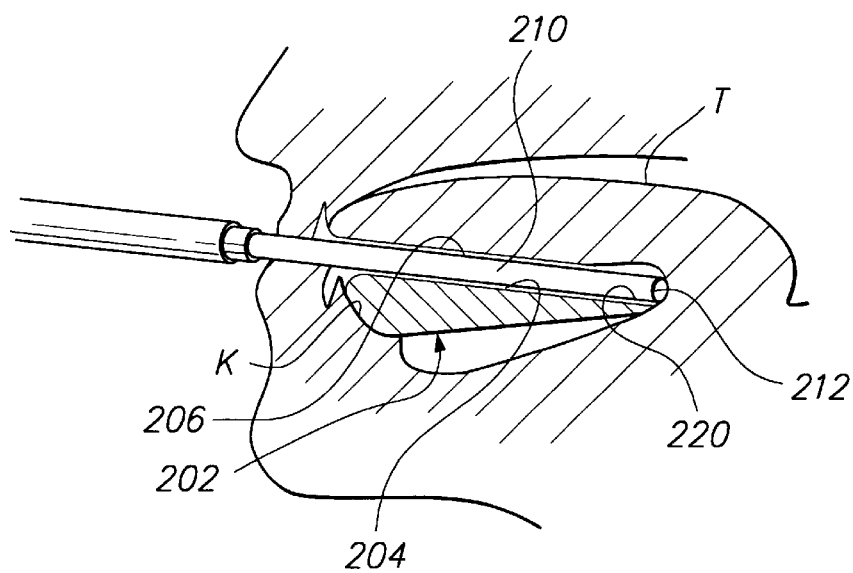
FIG. 12 is a sectional view of the holder of FIG. 11, shown lying in a patient's mouth, with a sensor assembly in place.

FIGS. 11 and 12 illustrate another holder 200 which applicants have designed. The holder basically includes a body 202 of plastic and preferably of elastomeric material, with an instrument passing passage in the form of a slot 204 in its upper surface 206. A short rigid tube 210 with a carbon dioxide sensor 212 can fit in the slot. A short rigid handle 214 extends outwardly from the tube, while a flexible cable 216 extends largely outwardly from the handle. The instrument is not longer than about ⅓rd meter.

FIG. 12 shows the body 202 lying completely in a person's mouth on the mouth floor at K, with the $CO_2$ sensor 212 lying against a mucosal surface area 220 that is sublingual. The tongue T of the person lies on the body upper surface 206 and seals the area directly behind the tongue. The body has a pair of opposite sides 222, 224 (FIG. 11) that project inwardly slightly more than the middle 226 to seal the opposite sides of the sensed area 220. The rest of the body seals the region under and outward of area 220. Only the tube 210 passes between the lips. It is possible for the holder and sensor to be fixed together, as with wires embedded in the body.

Figure 13:
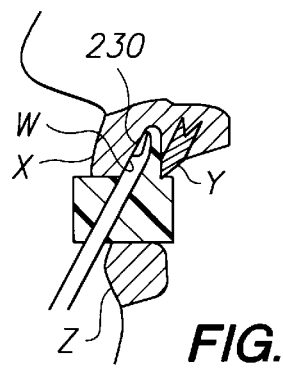
FIG. 13 is a sectional view of a sensor assembly and holder of another embodiment of the invention, shown holding a sensor between a lip and teeth of a patient.
Figure 14:
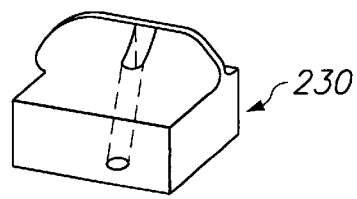
FIG. 14 is a front isometric view of the holder of FIG. 13.

Although applicant prefers to place the sensor in a sublingual area, it can be placed against other mucosal surfaces in the mouth or nose. As shown in FIG. 13, the sensor 230 can be placed at a mucosal surface W that lies between a lip X and the teeth Y of the person. The area at the rear of the upper or lower lips X, Z is a mucosal surface from which $CO_2$ is drawn by blood flow. FIGS. 13 and 14 show a holder 230, which is preferably of soft elastomeric material such as an elastomeric solid or a foam, or even a viscous fluid in a flexible shell. The holder isolates the mucosal surface area contacted by the sensor, from air flow, while preventing movement of the sensor, and to maintain close to 100% humidity.

Figure 15:
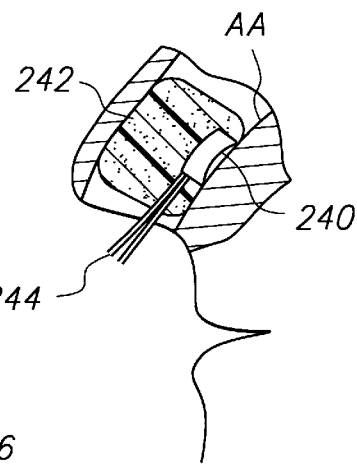
FIG. 15 is a sectional view of a sensor assembly and holder of another embodiment of the invention, shown holding a sensor in the nose of a patient.

FIG. 15 shows a $CO_2$ sensor 240 lying against a mucosal surface area AA in a naris (nostril) of a person's nose. A foam plug 242 serves as a holder that holds the sensor to position it, and that prevents air flow around the sensor. The foam plug can maintain close to 100% humidity. Only a pair of electrical wires 244 extend from the sensor through the holder.

Figure 17:
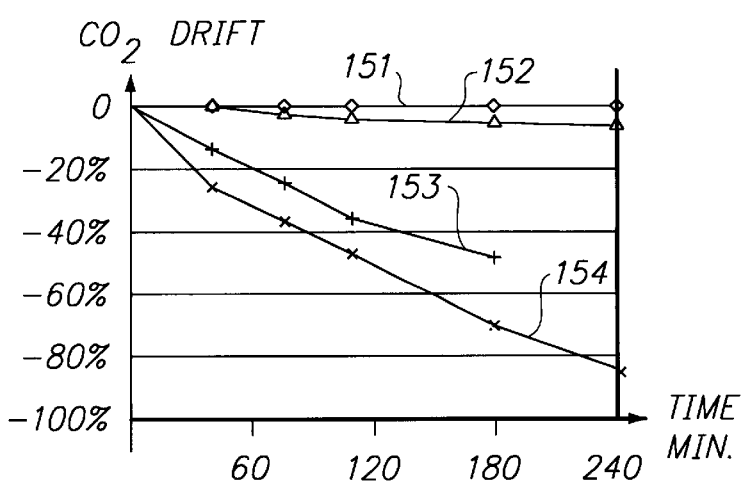
FIG. 17 is a graph showing $CO_2$ sensor drift with time in different environments.

Applicant has noted that $CO_2$ sensors tend to dry out during extended duration tests performed by applicant. This results in false readings that indicate a lower $CO_2$ level than is actually present. FIG. 17 shows $CO_2$ drift when sensors were placed in different environments during tests. Graph lines 151, 152, 153, and 154 respectively represent an environment of a 0.2% salt solution, human saliva, rat saliva, and air.

The two $CO_2$ sensors used by applicant were made, one by Microelectrode, Inc., and one by Nihon Kohden (ISFET $pCO_2$ sensor). Both sensors use a membrane that is permeable to $CO_2$, and that separate a sodium bicarbonate or carbonic acid ($HCO_3$) solution from the environment (a pH sensor measures the pH of the sodium bicarbonate solution). Moisture from the solution can pass out through the membrane to dry out the solution.

Figure 16:
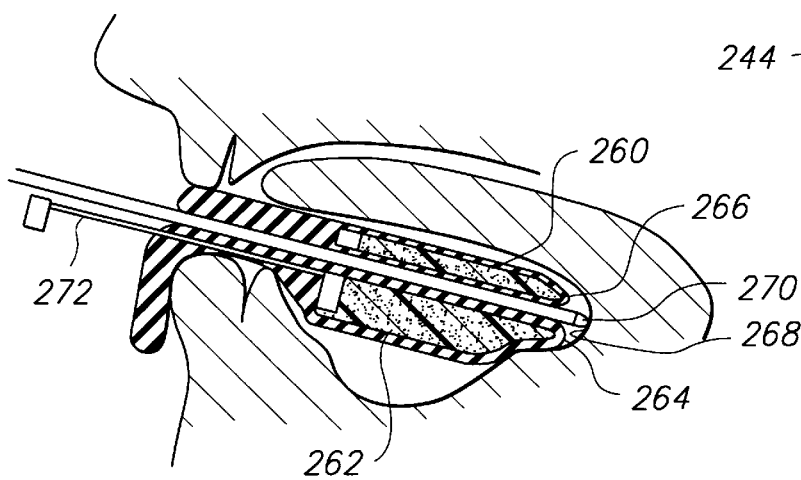
FIG. 16 is a sectional view of a sensor assembly and holder of another embodiment of the invention, where the holder can add moisture to the area of the sensor.

FIG. 16 shows a modified holder 260 which includes a sponge 262 containing a 0.2% salt solution (in water). Holes 264, 266 allow the weak solution to pass into the area 268 that is isolated by the holder, and where a $CO_2$ sensor 270 lies against a mucosal surface. A plunger 272 can be pushed to compress the sponge and introduce the weak salt solution to the area (volume) containing the sensor to prevent dryout. Instead, a tube can be used to pass water vapor into the area 268 from a humidifier.

Thus, the invention provides a method and apparatus for assessing perfusion failure, which causes minimal, or substantially no invasion of the patient, and which also can be quickly set up. The method includes introducing a carbon dioxide sensor into the upper digestive/respiratory tract of a patient, without passing the sensor down beyond the epiglottis where a first major intrusion would have occurred. Instead, the sensor is held against a mucosal surface in the upper digestive/respiratory tract while measurements of carbon dioxide are taken. The sensor is held against a mucosal surface of the mouth or nose, which includes the area under the tongue, an area between the upper or lower lip and the teeth, or an area in the nose. A holder prevents sensor movement, while isolating the sensor area from random air flow such as inspired and expired gases which would otherwise dilute the submucosal $CO_2$, and while maintaining high humidity. The invention is useful in triage in emergency and disaster settings, monitoring in anesthesia, intensive care, and other acute settings in which patients may have acute perfusion failure (shock).

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A method for assessing perfusion failure of a patient, comprising:

introducing a carbon dioxide sensor into the upper digestive/respiratory tract of the patient without passing the sensor down beyond the epiglottis, and holding the sensor against a mucosal surface in the upper digestive/respiratory tract while taking measurements of carbon dioxide by the sensor to assess perfusion failure of the patient.

2. The method described in claim 1, wherein:

said step of holding the sensor comprises holding the sensor under the tongue of the patient.

3. The method described in claim 1, wherein:

said step of holding the sensor comprises holding the sensor between a lip and teeth of the patient.

4. The method described in claim 1, wherein:

said step of holding the sensor comprises holding the sensor in a naris of the patient's nose while blocking the naris from the free flow of air therethrough.

5. The method described in claim 1, wherein:

said step of introducing includes placing a holder with inner and outer holder portions in the mouth of the patient, with said sensor mounted at said inner portion of the holder, and with said holder substantially sealing the area around said sensor to prevent the free flow of air thereby.

6. The method described in claim 1, including:

displaying the rate of change with time of carbon dioxide sensed by said sensor.

* * * * *